United States Patent
Itoh et al.

[11] Patent Number: 4,718,899
[45] Date of Patent: Jan. 12, 1988

[54] URINE ABSORBING AND HOLDING MATERIAL

[75] Inventors: Hiroshi Itoh; Atsuhiko Nitta, both of Yokohama; Tomio Tanaka, Tokyo; Hideo Kamio, Odawara, all of Japan

[73] Assignee: Mitsui Toatsu Chemicals, Incorporated, Tokyo, Japan

[21] Appl. No.: 782,452

[22] Filed: Oct. 1, 1985

[30] Foreign Application Priority Data

Oct. 11, 1984 [JP] Japan ................ 59-211246

[51] Int. Cl.$^4$ ............ A61F 13/16; A61F 13/18; A61F 13/20
[52] U.S. Cl. ............... 604/368; 604/375; 604/380; 523/111; 526/260; 526/263; 526/303.1; 526/304
[58] Field of Search ............... 604/368–380, 604/401; 523/111; 526/260, 263, 303.1, 304

[56] References Cited

U.S. PATENT DOCUMENTS

| Re. 25,645 | 9/1964 | Shields et al. | 526/303.1 |
| 2,790,789 | 4/1957 | Miller | 526/303.1 |
| 3,686,024 | 8/1972 | Nankee et al. | 604/368 |
| 3,714,946 | 2/1973 | Rudes | 604/401 |
| 3,903,890 | 9/1975 | Mesek et al. | 604/372 |
| 3,916,900 | 11/1975 | Breyer et al. | 604/373 |
| 3,936,441 | 2/1976 | Holst et al. | 604/368 |
| 3,965,091 | 6/1976 | Holst et al. | 604/368 |
| 4,000,028 | 12/1976 | Hoey | 604/372 |
| 4,058,124 | 11/1977 | Yen et al. | 523/111 |
| 4,066,828 | 1/1978 | Holst et al. | 604/368 |
| 4,068,067 | 1/1978 | Holst et al. | 604/368 |
| 4,079,739 | 3/1978 | Whitehead | 604/380 |
| 4,381,783 | 5/1983 | Elias | 604/378 |

Primary Examiner—C. Fred Rosenbaum
Assistant Examiner—Jerome R. Smith, Jr.
Attorney, Agent, or Firm—Oblon, Fisher, Spivak, McClelland & Maier

[57] ABSTRACT

Disclosed herein is a urine absorbing and holding material, which comprises a homopolymer of at least one monomer selected from specific N-alkyl- or N-alkylene-substituted acrylamides and methacrylamides, a copolymer of two or more of the acrylamides and methacrylamides, a copolymer of said at least one monomer with one or more monomers other the the acrylamides and methacrylamides and copolymerizable therewith, and being a water-insolubilized product. By combining the urine absorbing and holding material in the form of powder, granules, flakes, fibers or a film with a fibrous material in the form of a woven fabric, non-woven fabric or a flocculent material, a useful urea absorbing and holding composite material is obtained in the form of a pad, diaper or drawers.

11 Claims, 9 Drawing Figures

FIG. 3A PAD-LIKE URINE ABSORBING AND HOLDING MATERIAL

FIG. 3B

FIG. 4A
DIAPER-LIKE URINE ABSORBING AND HOLDING MATERIAL

FIG. 4B

FIG. 5A
DRAWERS-LIKE URINE
ABSORBING AND HOLDING
MATERIAL

URINE ABSORBING AND HOLDING MATERIAL

BACKGROUND OF THE INVENTION (a) Field of the Invention

This invention relates to a material for absorbing and holding urine. More specifically, it relates to a urine absorbing and holding material which has been rendered reusable by making a polymer of a specific (meth-)acrylamide derivative insoluble in water and then combining the water-insolubilized polymer with a fibrous material.

(b) Description of the Prior Art

Diapers have been widely used for many years as materials for absorbing and holding urine. Reflecting the significant prolongation in the average span of human life and the rapid advancement in the medical technology in recent years, there are more and more people who are bedridden or are forced to live with physical handicap such as walking difficulties or hardship. There is a ever-increasing demand for the materialization of welfare society for all people inclusive of such handicapped people.

Specifically speaking, it is desired to allow such people to have life similar to the life style of healthy people. For this purpose, various care or nursing aids, materials, equipment and systems have been developed. However, there are some difficult problems which are still waiting for solutions. As one of such unsolved problems, there is a problem regarding how urination should be dealt with.

Namely, it is a difficult problem for bedridden patients admitted in hospitals or the like how to deal with their urination at night. For those having difficulties or hardship in walking, it is a serious problem how they should deal with sudden desire of urination. This unsolved problem leads to unpleasant feeling after the incontinence of urine. It is also believed to become one of causes for diseases such as cold if the spilled urine is left over especially in winter. To cope with this problem, it has been practiced to spread pads over beds to absorb urine or to use large diapers. Such materials are however not fully satisfactory, because they do not have sufficient urine absorbing and holding capacity and the once-absorbed urine is released by pressures such as users' body weights. It has recently been attempted to enhance the urine absorbing and holding capacity by incorporating a hygroscopic resin such as a water-insolubilized product of a polyacrylate salt in such pads or diapers. Although this approach is certainly effective for enhancing the urine-holding capacity, it is difficult to separate water from the wet resin when the used pads or diapers are used repeatedly. Due to this difficulty, it is practically impossible to use such pads or diapers repeatedly. This means that they have to be thrown away once they have been used, resulting in more expenses for them.

SUMMARY OF THE INVENTION

An object of this invention is to provide a urine absorbing and holding material which has large urine absorbing and holding capacity and especially, facilitates its regeneration upon its repeated utilization.

Another object of this invention is to provide a urine absorbing and holding material which permits easy release of water upon its regeneration and has excellent drying readiness.

A further object of this invention is to provide a urine absorbing and holding material from which the absorbed and held urine components are promptly released into water so as to permit its easy washing.

A still further object of this invention is to provide a urine absorbing and holding composite material of excellent quality through the combination of a urine absorbing and holding material of this invention and another material.

The above-described objects of this invention have been fulfilled by the provision of the following material:

A material for absorbing and releasing urine, comprising a homopolymer of at least one monomer selected from N-alkyl- or N-alkylene-substituted (meth)acrylamides represented by the following general formula (I) or (II):

wherein $R_1$ means a hydrogen atom or methyl group, $R_2$ denotes a hydrogen atom or methyl or ethyl group, and $R_3$ is a methyl, ethyl or propyl group, or wherein $R_1$ means a hydrogen atom or methyl group and A denotes $-(CH_2)_n$ (n: 4–6) or $-(CH_2)_2O-(CH_2)_2-$, a first copolymer of two or more monomers selected from the N-alkyl- or N-alkylene-substituted (meth)acryl-amides, or a second copolymer of at least one monomer selected from the N-alkyl- or N-alkylene-substituted (meth)acrylamides and one or more monomers other than the N-alkyl- or N-alkylene-substituted (meth)acryl-amides and copolymerizable with the N-alkyl- or N-alkylene-substituted (meth)acrylamides; and being a water-insolubilized product of the homopolymer or the first or second copolymer.

By combining the above-described urine absorbing and holding material with a suitable fibrous material into a composite material, it may be used as a pad-like material which can be regenerated for its repeated use and can hence meet application purposes of this invention.

DETAILED DESCRIPTION OF THE INVENTION

Figure 1:
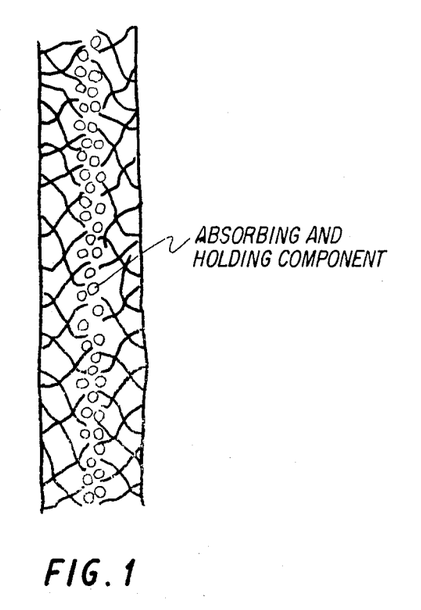
FIG. 1 shows a plan view of the device.
Figure 2:
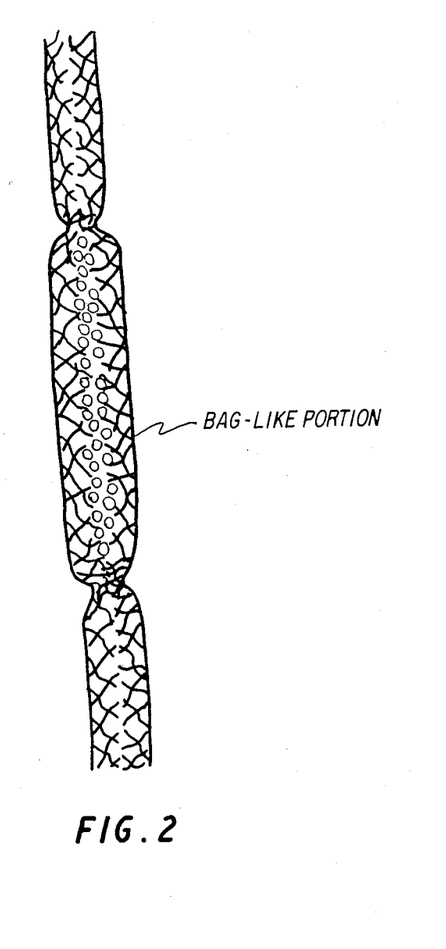
FIG. 2 shows a plan view of a modified form of the device.
Figure 3A:
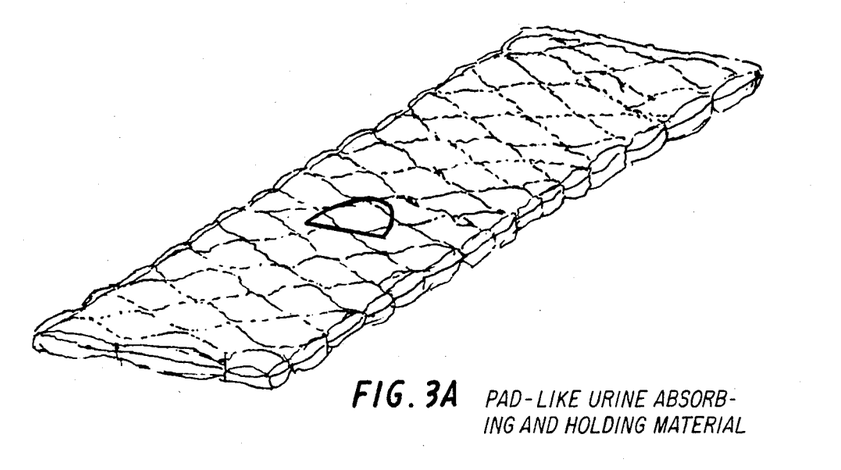
FIG. 3A shows a perspective view of the device.
Figure 3B:
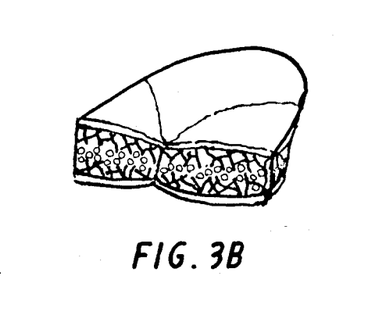
FIG. 3B shows a sectional view of FIG. 3A.
Figure 4A:
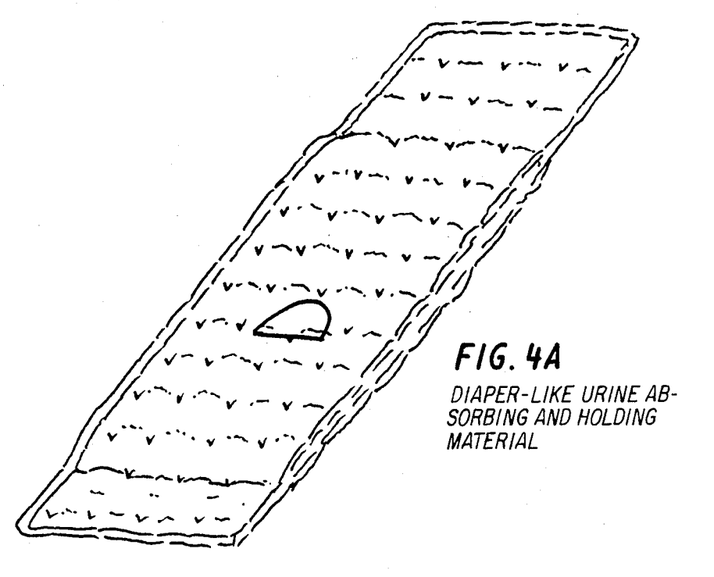
FIG. 4A shows a perspective of another modification of the device.
Figure 4B:
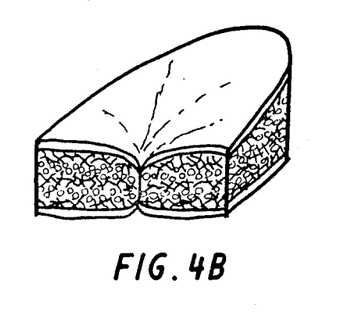
FIG. 4B shows a sectional view of FIG. 4A.
Figure 5A:
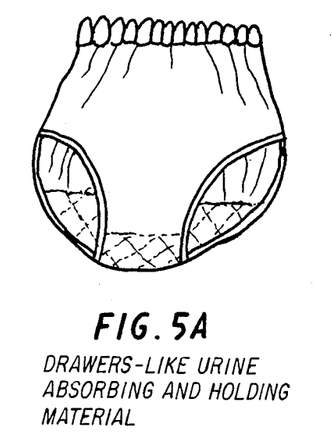
FIG. 5A shows a perspective front view of a garment using the device.
Figure 5B:
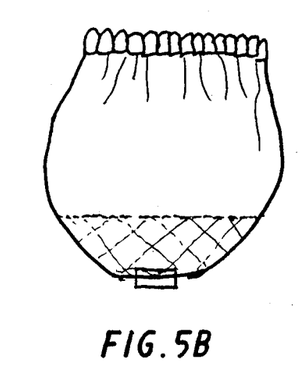
FIG. 5B shows a rear view of FIG. 5A.
Figure 5C:
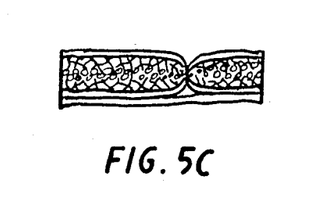
FIG. 5C shows a sectional view of the device used in FIG. 5A.

The following procedure may be followed to prepare the urine absorbing and holding material, which is a water-insolubilized product of a polymer or copolymer of at least one of specific N-alkyl- or N-alkylene-substituted (meth)acrylamides useful in the practice of this invention.

As examples of the above-described polymer and copolymers, may be mentioned polymers and copolymers of at least one of the following N-alkyl- or N-alkylene-substituted acryl and methacryl amides:
N-n-Propylacrylamide;
N-n-Propylmethacrylamide;
N-Isopropylacrylamide;
N-Isopropylmethacrylamide;
N-Ethylacrylamide;
N,N-Diethylacrylamide;
N-Ethylmethacrylamide;
N,N-Dimethylacrylamide;
N,N-Dimethylmethacrylamide;
N,N-Diethylmethacrylamide;
N-Methyl-N-ethylacrylamide;
N-Methyl-N-ethylmethacrylamide;
N-Acryloylpyrrolidine;
N-Methacryloylpyrrolidine;
N-Acryloylpiperidine;
N-Methacryloylpiperidine;
N-Acryloylmorpholine; and
N-Methacryloylmorpholine.

Among the above-described compounds, the N,N-dialkyl-substituted (meth)acrylamides are preferred for the preparation of urine absorbing and holding materials of this invention. More preferred compounds are the N-alkylene-substituted (meth)acrylamides in each of which the two alkyl groups substituted to the amido group are combined together at their terminals to form a cyclic structure. Specifically, N-(meth)acryloylpyrrolidines and N-(meth)acryloylpiperidines are particularly preferred. The polymers, which are obtained by making the above-described N-alkylenesubstituted (meth)acrylamide polymers insoluble in water, feature that the reductions to their water-absorbing capacity in electrolytic aqueous solutions are extremely small compared with their water-absorbing capacity in pure water.

In addition, one or more monomers selected from for example hydrophilic monomers, ionic monomers and hydrophobic monomers may additionally be copolymerized.

As exemplary hydrophilic monomers, may be mentioned acrylamide, methacrylamide, N-methylacrylamide, diacetoneacrylamide, hydroxyethyl methacrylate, hydroxyethyl acrylate, hydroxypropyl methacrylate, hydroxypropyl acrylate, various methoxypolyethyleneglycol acrylates, various methoxypolyethyleneglycol acrylates, and N-vinyl-2-pyrrolidone. Further, vinyl acetate or glycidyl methacrylate for example may be introduced by copolymerization, followed by hydrolysis to impart hydrophilicity.

Illustrative of such ionic monomers are acids such as acrylic acid, methacrylic acid, vinylsulfonic acid, allylsulfonic acid, methallylsulfonic acid, styrenesulfonic acid, 2-acrylamido-2-phenylpropanesulfonic acid and 2-acrylamido-2-methyl-propanesulfonic acid and their salts; amines such as N,N-dimethylaminoethyl methacrylate, N,N-diethylaminoethyl methacrylate, N,N-dimethylaminoethyl acrylate, N,N-dimethylaminopropyl methacrylamide and N,N-dimethylaminopropylacrylamide and their salts. Further, it is also possible to impart ionic properties by introducing various acrylates, methacrylates, acrylamides, methacrylamides or acrylonitriles by copolymerization and then hydrolyzing the thus-introduced moieties.

As hydrophobic monomers, may for example be mentioned N-alkylacrylamide derivatives and N-alkylmethacrylamide derivatives such as N-n-butylacrylamide, N-n-butylmethacrylamide, N-tert-butylacrylamide, N-tert-butylmethacrylamide, N-n-hexylacrylamide, N-n-hexylmethacrylamide, N-n-octylacrylamide, N-n-octylmethacrylamide, N-tert-octylacrylamide, N-n-dodecylacrylamide, N-n-dodecylmethacrylamide and the like; N-(ω-glycidoxyalkyl)acrylamide derivatives and N-(ω-glycidoxyalkyl)methacrylamide derivatives such as N,N-diglycidylacrylamide, N,N-diglycidylmethacrylamide, N-(4-glycidoxybutyl)acrylamide, N-(4-glycidoxybutyl)methacrylamide, N-(5-glycidoxypentyl)acrylamide, N-(6-glycidoxyhexyl)acrylamide and the like; acrylate derivatives and methacrylate derivatives such as ethyl acrylate, methyl methacrylate, butyl methacrylate, butyl acrylate, lauryl acrylate, 2-ethylhexyl methacrylate and glycidyl methacrylate; acrylonitrile; methacrylonitrile; vinyl acetate; vinyl chloride; olefins such as ethylene, propylene and butene; styrene; α-methylstyrene; butadiene; and isoprepene.

The acceptable proportion of such a hydrophilic, ionic or hydrophobic monomer to the acrylamide or methacrylamide derivatives may vary depending on the combination of the acrylamide or methacrylamide derivative and the above-mentioned monomer. Although not sweepingly applicable to every combination, the hydrophilic, ionic and hydrophobic monomers may generally be used in amounts of 60 wt. % or less, 30 wt. % or less and 60 wt. % or less, respectively.

As a method for water-insolubilizing polymers of the above-mentioned monomers, they may be insolubilized upon their polymerization or by treating them subsequent to their polymerization.

As specific insolubilizing methods, the following various methods may be employed:

(1) to copolymerize a crosslinkable monomer containing at least two double bonds per molecule with the above-described acrylamide or methacrylamide derivatives;

(2) to copolymerize the polymer with N-alkoxymethyl(meth)acrylamide derivatives;

(3) to increase the proportion of the above-mentioned hydrophobic monomer and to copolymerize it with acrylamide or methacrylamide derivatives;

(4) to effect polymerization by the bulk polymerization method;

(5) to subject the polymer to a heat treatment;

(6) to integrate the polymer with a water-insoluble fibrous material such as cellulose;

(7) when the polymer contains for example hydroxyl or amino groups, to couple such groups with a polyfunctional compound such as epichlorohydrin to insolubilize the polymer; and (8) to copolymerize the monomer represented by the general formula (I) with a monomer containing a substituent group such as carboxyl group, sulfo group or hydroxyl group having at least one active hydrogen atom, or to form the polymer of the monomer represented by the general formula (I) and a polymer of the above monomer into a polymer complex, thereby insolubilizing the polymer.

The above insolubilizing methods will next be described more specifically.

In the first method, it is possible to use as exemplary crosslinkable monomers N,N'-methylenebisacrylamide, N,N-diallylacrylamide, triacrylic formal, N,N-diacryloylimide, N,N-dimethacryloylimide, ethyleneglycol diacrylate, ethyleneglycol dimethacrylate, various polyethyleneglycol diacrylates, various polyethyleneglycol dimethacrylates, propyleneglycol diacrylate, various polypropyleneglycol diacrylates, various polypropyleneglycol dimethacrylates, 1,3butyleneglycol diacrylate, 1,3-butyleneglycol dimethacrylate, 1,4-butyleneglycol dimethacrylate, glycelol dimethacrylate, neopentylglycol dimethacrylate, trimethylolpropane triacrylate, trimethylolpropane trimethacrylate, trimethylolethane trimethacrylate, trimethylolethane triacrylate, tetramethylolmethane tetramethacrylate, tetramethylolmethane triacrylate, divinylbenzene and diallyl phthalate. The proportion of each of these crosslinkable monomers to the above described acrylamide derivative may vary depending on the combination of the acrylamide derivative and crosslinkable monomer as well as the desired crosslinking degree Although not applicable sweepingly to every situation, the crosslinkable monomers may each be used in an amount of 0.01-10 wt. %.

N-Alkoxymethyl(meth)acrylamide derivatives useful in the practice of the second method may include N-hydroxymethyl(meth)acrylamides. For example, N-methylol(meth)acrylamides, N-methoxymethyl(meth)acrylamides, N-ethoxymethyl(meth)acrylamides, N-n-butoxymethyl(meth)acrylamides and N-tert-butoxymethyl(meth)acrylamides may be used. The proportion of each of such N-alkoxymethyl(meth)acrylamide derivatives to the above-described acrylamide derivatives may vary depending on the combination of the acrylamide derivatives and the N-alkoxymethyl(meth)acrylamide derivatives. Although not applicable sweepingly to every combination, the N-alkoxymethyl(meth)acrylamide derivatives may each be used generally in an amount of 0.01-30 wt. %.

In the third method, the proportion of the hydrophobic monomer to the (meth)acrylamide derivative having amphiphilic property may vary depending on the combination of the (meth)acrylamide derivative and the hydrophobic monomer. Although not conclusively limitable, the proportion of the hydrophobic monomer may generally be 1 wt. % or more, or preferably 3 wt. % or more. In this case, the copolymerization may be effected using one of the random copolymerization method, block copolymerization method or graft copolymerization method.

In the fourth method, the polymerization is carried out by the bulk polymerization method. This may be practiced by polymerizing the monomer as is without diluting it with any solvent to obtain a polymer block or by suspending the monomer in a solvent and then effecting the polymerization of the monomer in the form of droplets so as to obtain a granular polymer.

In the fifth method, the polymer is subjected to a heat treatment. The heating conditions may vary depending on the polymer and do not remain constant. However, a polymer obtained by for example bulk polymerization, suspension polymerization or solution polymerization is heat-treated generally at 60°-250° C., or preferably at 80°-200° C. In this case, when the polymer is obtained by the solution polymerization method, its heat treatment may be carried out concurrently with its drying or with the evaporation of the solvent.

Turning to the sixth method in which the polymer is integrated with for example a fibrous material, the above-described (meth)acrylamide derivative may be impregnation- or graft-polymerized to a water-insoluble fibrous material such as natural or synthetic fibers such as cellulose fibers, nylon fibers, polyester fibers or acrylic fibers or non-woven fabric made of polypropylene or an ethylene-propylene copolymer, or to a water-insoluble porous material such as silica, alumina or zeolite. Alternatively, the fibrous or porous material may be impregnated with the polymer.

In the seventh method, the polyfunctional compound such as epichlorohydrin is reacted with the polymer so that the polymer is crosslinked and insolubilized. In this method, it is necessary to introduce hydroxyl, amino or carboxy groups in advance in the polymer. Amino and carboxy groups can be introduced readily by copolymerization. In the case of hydroxyl groups, they may be introduced by copolymerization hydroxyethyl methacrylate, isopropenyl phenol by first introducing for example vinyl acetate or glycidyl methacylate by the copolymerization method and then saponifying it with a basic material to form hydroxyl groups. Thereafter, the above-prepared polymer and a polyfunctional compound such as epichlorohydrin are reacted to each other in the presence of a basic material so as to crosslink and insolubilize the polymer. When the polymer is insolubilized in an aqueous solution as is, it is converted into an agar-like state. By simply crushing the thus-obtained polymer, it can be used immediately. If it is solubilized after dispersing the aqueous solution in an oil, granular gels are obtained.

According to the eighth method, a polymer complex is formed by copolymerizing the polymer with the above-described monomer containing an active hydrogen or by combining the polymer with a copolymer of such a monomer. In this case, it is also possible to form a polymer complex by regeneration of the active hydrogen atoms of the copolymer which are substituted with ammonium ions or the like on mixing with the other component of the polymer by the addition of an acid then adding an acid to activate the active hydrogen atoms.

The above-described eight methods may be used singly or in combination. Generally speaking, more effective results are obtained when two or more of these methods are used in combination.

As more specific polymerization methods which may be used upon production of urine absorbing and holding materials of this invention in accordance with the above-mentioned methods, the following polymerization methods may be mentioned by way of example:

(1) to polymerize a monomer as is without diluting it in a solvent and to produce a polymer block;

(2) after polymerizing in a solvent, to dry the resultant polymer or to cause the polymer to precipitate in a bad solvent, thereby obtaining the polymer;

(3) to obtain the polymer as a granular polymer in accordance with the suspension polymerization method;

(4) to obtain the polymer as a polymer latex in accordance with the emulsion polymerization method; and (5) to integrate the polymer with a water-insoluble fibrous material or porous material by impregnation- or graft-polymerizing a solution of the polymer to the water-insoluble fibrous material or porous material.

As solvents usable upon polymerization in the method (2), it is possible to use a variety of solvents because (meth)acrylamide and their N-substituted derivatives have very good miscibility with such various solvents. More specifically, may be mentioned water, alcohols such as methanol and ethanol, cyclic ethers such as tetrahydrofuran and 1,4-dioxane, ketones such as acetone, amides such as N,N-dimethylformamide and N,N-dimethylacetamide, aromatic hydrocarbons such as benzene and toluene, halogenated hydrocarbons such as chloroform and methylene dichloride, chain glycols such as dimethyl sulfoxide, N-methylpyrrolidone, diglyme and tetraglyme, basic solvents such as pyridine, etc.

In the above specific polymerization methods, the polymerization may be initiated only by heating the polymerization systems. However, use of a polymerization initiator can generally bring about better results. No limitation is imposed on the polymerization initiator. Any polymerization initiators may be used so long as they can initiate radical polymerization. For example, inorganic peroxides, organic peroxides, combinations of such peroxides and reducing agents, and azo compounds may be mentioned. More specifically, such polymerization initiators may include ammonium persulfate, potassium persulfate, hydrogen peroxide, tert-butyl peroxide, benzoyl peroxide, cumenehydroxy peroxide, tert-butylperoxy-2-ethyl hexanoate, and butyl perbenzoate. As reducing agents which may be used in combination with such polymerization initiators, may be mentioned sulfites, hydrogensulfites, salts of lower valence metals such as iron, copper and cobalt, organic amines such as aniline and reducing sugars such as aldose and ketose. Usable azo compounds may include azobisisobutylonitrile, 2,2'-azobis-2-amidinopropane hydrochloride, 2,2'-azobis-2,4-dimethylvaleronitrile and 4,4'-azobis-4-cyanovaleric acid. Two or more of the above-described polymerization initiators may be used in combination. In this case, the amount of the polymerization initiator to be added may be within the commonly-employed amount range, for example, may be within the range of 0.01–5 wt. %, or preferably 0.05–2 wt. %, both based on the monomer.

Among the thus-obtained polymers, the block-like polymer or the polymer obtained after evaporation of the solvent may be crushed into a powdery material or may be melted and then formed into a flake-, fiber- or film-like material. The granular polymer may be provided as a granular material without need for any further processing. The latex-like polymer may be provided to impregnate and coat a fibrous or porous material such as fabric or paper or may be formed into films to provide a urine absorbing and holding material.

A powdery product may be obtained by various methods as described above, for example, by conducting gel polymerization in an aqueous solution and then drying and grinding the resultant polymer. A granular product may generally be produced with ease in accordance with the suspension polymerization method. Since the N-alkyl- or N-alkylene-substituted (meth)acrylamide derivative has generally high solubility in water, suspension polymerization may be practiced as the reversed phase suspension technique in which a monomer or its aqueous solution is dispersed in an oil, as the salted-out suspension polymerization technique in which an electrolyte is dissolved in a large amount in an aqueous solution to reduce the solubility of a monomer, or as the precipitation and suspension polymerization technique in which polymerization is carried out at an elevated temperature of the cloud point of the intended polymer or higher so as to cause the polymer to precipitate. In addition, it is also possible to integrate the polymer with porous beads such as silica, alumina or zeolite, for example, by impregnating the porous beads with a solution of the polymer or effecting graft polymerization on such porous beads. It is also possible to incorporate a third component miscible with the monomer or monomers but immiscible with the resulting polymer when conducting polymerization in accordance with one of the above-mentioned polymerization techniques. Incorporation of such a third component permits production of a porous resin.

The urine absorbing and holding material prepared in the above manner is in a solid form and has extremely unique properties that it absorbs and holds water upon its contact with an aqueous solution but when heated in the presence of a large excess of water, it shrinks and releases that water. As a still more convenient feature, the above-described process of water absorption and holding and its release can be repeated.

The amount of water, which the above material can absorb, varies depending on the composition of the polymer (hereinafter abbreviated merely as "the resin") obtained by water-insolubilizing the polymer or copolymer of its corresponding at least one of the N-alkyl- or N-alkylene-substituted (meth)acrylamides useful in the practice of this invention, the temperature at the time of water absorption, the composition of each aqueous solution, etc. Dealing with the resin composition, in the case of a copolymer with a hydrophobic monomer out of the above-described copolymerizable monomers, the amount of absorbable water decreases but the mechanical strength of the resin increases as the proportion of the hydrophobic monomer increases. In the case of a copolymer with either hydrophilic or ionic monomer, the amount of absorbable water itself increases as the proportion of the hydrophilic or ionic monomer increases. However, the amount of absorbable water becomes less dependent on the temperature and the mechanical strength of the polymer decreases as the proportion of the hydrophilic or ionic monomer becomes higher. The amount of absorbable water by each resin changes in accordance with the composition of the resin as mentioned above. At room temperature (25° C.), the resin can generally absorb water as much as about 2–100 times its own weight. More water can be absorbed if the temperature is lowered.

Furthermore, the resin has a property extremely convenient as a urine absorbing and holding material that the resin shrinks and releases the water when its temperature is raised subsequent to its water absorption. When the temperature of the resin is raised further, the shrinkage of the resin may become extremely little beyond a certain temperature. In other words, a transition point may be observed as to its shrinking phenomenon. This transition point is determined by the composition of each resin. It may generally be controlled within the range of 10°–100° C. The degree of shrinkage of each resin around its transition point may vary depending on the composition of the resin, the composition of each aqueous solution and the like, it is usually about 1 to 20 times its own weight. After allowing the resin to absorb urine in an amount as much as about 20 times its own weight, the resin may thus be subjected to washing, heating and removal of accompanying water to reduce its holding water to an amount about 5 times its own weight and the resin may then be dried, if necessary or desired.

On the other hand, low molecular weight substances such as inorganic salts, organic salts, water-soluble organic substances and the like are dissolved in urine. The urine absorbing and holding material of this invention can take urine into its resin as is, namely, as an aqueous solution with such substances contained therein. If inorganic salts are contained in their dissolved forms, conventional water-absorbing resins showed remarkable reductions to the amounts of water which they were able to absorb. For example, in the case of an acrylamide-sodium acrylate copolymer (content of sodium acrylate: 21 wt. %) crosslinked by methylenebisacrylamide, the amount of absorbable water drops to one seventeenth in a 1N aqueous solution of sodium chloride compared with the amount of its absorbable water in distilled water. On the other hand, the percent reduction of absorbable water is around 10% in the case of the urine absorbing and holding material of this invention. Therefore, the amount of absorbable water is little affected by concomittant substances in urine. This means that the urine absorbing and holding material of this invention can achieve the same level of urine-absorbing effects in a resin amount smaller than a conventional hygroscopic resin provided that the amounts of pure water, which they can absorb respectively, are equal. This feature is particularly effective when the urine absorbing and holding material of this invention is repeatedly used, because the difference between the degree of its swelling in urine and that at the time of its washing is small and substantially no additional water is hence absorbed at the time of its washing.

In the case of such a conventional water-absorbing resin, it is thus necessary for absorbing the same amount of water to add it in an amount as much as at least 20–30 times when applied to urine compared with pure water. As a result, the resin volume increases considerably during its washing due to absorption of water by the resin. This becomes a serious problem in using this conventional resin repeatedly.

As has been described above, the urine absorbing and holding material of this invention absorbs urine in a dry state. Thereafter, it is washed and if necessary, is subjected to removal of accompanying water. The resin is then dried for its regeneration, preferably, by exposing it to an atmosphere of an elevated temperature. In view of the temperature of the surrounding atmosphere, the temperature of urine is within the range of 0°–40° C. at the time of urine absorption. In order to heat the water-absorbed resin so to cause the resin to undergo shrinkage subsequent to its washing on the other hand, it is only necessary to exposure it to an atmosphere of a high temperature. This may be achieved in air, in hot water, or by means of a heating device such as iron, press or the like. Although the heating temperature varies depending on the atmosphere, a relatively low temperature may be used where the heating device or atmosphere has a large capacity. In the opposite case, higher temperatures are preferred. It may generally be 30°–200° C., preferably 40°–120° C., and more preferably 50°–90° C.

The above-described absorption and holding of urine and the above-mentioned release of water and drying under heat appear to proceed conveniently, because the resin of this invention has been confirmed by electron-microscopic pictures to form a honeycomb structure of minute cells and it can thus maintain "a porous aqueous gel structure".

As a specific method for achieving the absorption and holding of urine, it is only necessary to bring the resin into contact with urine. For this purpose, the absorbing and holding material may take any one of powdery form, granular form, flaky form, fibrous forms (inclusive of woven fabric and non-woven fabric), film-like form and the like. These absorbing and holding materials may be used either as they are or after combining them with other materials into composite materials. Although both of the above application forms can be employed, the composite forms are preferred for effecting efficient absorption and holding of urine and for achieving prompt drying upon repeated utilization. As such composite materials, may be mentioned those obtained by combining the urine absorbing and holding materials of the above-described forms (hereinafter abbreviated as "the above material or materials") with a variety of fibrous materials into composite materials, those obtained by integrating various fibrous materials and the above materials in accordance with such a method as impregnation, graft polymerization or the like and then processing them into woven fabrics or non-woven fabrics, and those obtained, on the contrary, by integrating woven fabrics or non-woven fabrics with the above materials in accordance with such a method as impregnation, graft polymerization or the like, and those obtained by combining the above procedures.

As the above-described fibrous material, natural fibers, semi-synthetic fibers and synthetic fibers are all usable. Specific examples of the fibrous material may include, for example, cotton, hemp, silk, acetate rayon, cuprammonium rayon, viscose rayon, pulp, acrylic fibers, nylon, vinylidene fibers, vinylon, fluorocarbon fibers, promix fibers, polyurethane fibers, polyester fibers, polyethylene fibers, polyvinyl chloride fibers, polypropylene fibers, asbestos, glass fibers, silica fibers, carbon fibers, and so on. They may be filaments or staples. They may be in any of the forms of woven fabrics, non-woven fabrics, flocculent materials like cotton wool (hereinafter abbreviated as "flocculent material or materials") and pulplike materials. These materials may be used in combinations.

As the simplest specific method for combining the fibrous material and the above material into a composite material, may be mentioned to sandwich the above material between the entire areas or some areas of layers of woven or non-woven fabrics, and then to sew the thus-combined material and fabrics or to unite them together by pressure or heat. Here, a flocculent material, pulplike material, non-woven fabrics or the like may be interposed between the material and the non-woven or woven fabrics in order to prevent movement of the material and to soften the resulting composite material. As a more specific method for combining the above material and the fibrous material into a composite material, the above material is spread or distributed on or in the fibrous material. Alternatively, one or more parts of the fibrous material are formed into one or more pockets or bags, in which the above material is then filled. In some instances, the above material may be sandwiched by the fibrous material. Thereafter, the thus-combined materials are sewn or applied with pressure or heat to unite them together. As a sewing method, quilting or the like may be mentioned. As a unification method making use of pressure or heat, the combined materials may be pressed while heating their surfaces uniformly or the combined materials may be heated locally so as to subject them to spot or line melt-bonding.

In the above method, the amount of the above material to be used in combination with the fibrous material varies depending on the application purpose of the resulting composite material and application conditions. If the amount of the above material added to the fibrous material is too little, the amount of urine to be absorbed in the resulting composite material will be little. Thus, the resulting composite material will not be able to any noticeable effect. If the amount is too much on the other hand, the volume of the above material will change considerably as urine is being absorbed. As a result, some inconvenience will be developed, for example, the united composite material will be broken. The amount of the above material may generally be used in an amount of 2 g/m$^2$–2,000 g/m$^2$ or preferably 5 g/m$^2$–1,000 g/m$^2$ per every layer of the fibrous material or for the entire layers of the fibrous material.

As a method for integrating the above material with one of various fibrous materials by impregnation, graft polymerization or the like and then processing the thus-combined materials into woven or non-woven fabrics, an N-alkyl or N-alkylene-substituted (meth)acrylamide is polymerized in the presence of the above-described material. The resultant homopolymer, first copolymer or second copolymer is insolubilized either separately if necessary or simultaneously with its formation so that the above material and the fibrous material are united together. Thereafter, the thus-united materials are formed into a woven or non-woven fabric by a method known per se in the art.

As a method for uniting the above material with one or more woven or non-woven fabrics by impregnation, graft polymerization or the like, the above-described homopolymer, first copolymer or second copolymer is produced in the presence of the woven or non-woven fabrics in the same manner a described above. The homopolymer, first copolymer or second copolymer is insolubilized either separately if necessary or simultaneously with its formation. More firmly-united composite materials may also be produced by conducting spinning or forming non-woven fabrics in the presence of the above material.

The application form of the above described composite material, which is formed of the above material and the fibrous material, varies depending on its user. Namely, for completely-bedridden people, it may be used as sheet-like pads to be spread between their beds and their lap areas or as diapers. In the case of people capable of moving their bodies to some extents, it may be used as diapers or drawers-like underwear (hereinafter abbreviated as "incontinence drawers"). For those capable of going out but having difficulties or hardship in walking, it may be provided as incontinence drawers.

More specifically, a sheet-like pad may be provided by dispersing the above material in a fibrous material such as woven fabrics, non-woven fabrics, flocculent material or the like or in a combination of such fabrics and/or materials to combine them together and then sewing the thus-combined materials or applying pressure or heat to them so as to unite them together. A diaper is formed by making the above-described pad thinner and cutting the resultant thin sheet. A pair of incontinence drawers may be formed in the following manner. Namely, the above-described pad is made thinner. By using the resultant sheet as a cloth, it is sewn into an underwear like drawers. Alternatively, the cloth is used only for a desired area and a usual fabric such as knit cloth is employed for the remaining area. They are then sewn into an underwear like drawers. In both of the above-described cases, moisture-permeable waterproof films or fabrics may be used to avoid leakage of urine to the outside. As such waterproof films or fabrics, it is possible to use, for example, breathable polyolefin films, those obtained by laminating microporous fluorocarbon films or the like with woven fabrics, knit materials or the like, those obtained by coating woven fabrics, knit materials or the like with a polyurethane resin or the like, those formed by weaving ultrafine fibers into high densities, etc.

As its application method, the waterproof film or fabric may be simply brought into contact with one side of the composite material of the above material and fibrous material, said side being opposite to the side where the composite material is kept in contact with the human body while in use. Alternatively, the waterproof film or fabric may have dimensions somewhat larger the corresponding composite material and the outwardly-extending portions of the waterproof film or fabric may be folded inwardly. Here, the form of the above material varies depending how the resulting composite material is used. When it is desired to absorb urine promptly, it is preferably for the above material to have a relatively large specific surface area. When it is desired to hold urine firmly on the other hand, the above material is used with a relatively large grain size. After absorbing and holding urine in the above manner, the composite material is washed usually in a washing machine or the like to remove the urine By the washing, the amounts of urine components still remaining in the above material can be reduced to ignorable levels. This is extremely convenient from the viewpoint of assurance of sanitation. Furthermore, accompanying water may be removed by centrifugation or the like if necessary.

Then, the thus-washed composite material which contains the above material is exposed to the above-described elevated temperature. The water is readily caused to evaporate, thereby drying the composite material. As a specific method for practicing the above drying, a usual hot air drier may be used. The composite material may be heated, for example, by blowing steam against the same, immersing it in hot water or pressing it under heat with an iron, hot rolls or the like, whereby the water is released as liquid and the above material is thus caused to shrink. Thereafter, the composite material is heated to have any remaining water evaporate as water vapor so that it is dried. The thus-regenerated composite material may be repeatedly used as a urine absorbing and holding composite material as many times as desired.

(1) Since the above-described urine absorbing and holding material of this invention can release water in its liquid form without undergoing any phase change by its mere heating, it can be promptly dried after its washing. Thus, its regeneration operation can be carried out with ease. (2) When it is dispersed in water after absorbing and holding urine in its honeycomb structure, urine components are allowed to diffuse promptly into the water. It is thus easy to wash off such urine components from the above material in the washing step. This feature is extremely convenient from the standpoint of sanitation. (3) Since the difference between its swollen volume upon absorbing and holding urine and that upon absorbing and holding water is small, in other words, it is affected little by the presence of inorganic salts, its volume change between the urine absorbing step and the washing step is small. The above material has thus brought about another advantageous effect that the damages to the final product due to its volume changes upon its repeated use can be minimized.

The above-described urine absorbing and holding material, especially, the urine absorbing and holding composite material is one of especially-useful care or nursing aids for those bedridden or forced to live with physical handicap such as walking difficulties or hardship. It is also useful as an auxiliary material when infants start to wear drawers instead of diapers.

REFERENTIAL EXAMPLE 1

Respectively placed in graduated cylinders, each filled with 50 ml of distilled water, were 1.0 g portions of powder samples employed in Examples which will be described herein. Their equilibrium water absorptions were measured at 25° C. and 50° C. in terms of volumes in their corresponding graduated cylinders.

| Example No. | Water absorption (ml/g) | |
|---|---|---|
| | 25° C. | 50° C. |
| 1 | 17.5 | 7.0 |
| 2 | 17.5 | 7.0 |
| 4 | 19.5 | 11.5 |
| 5 | 14.0 | 5.0 |
| 6 | 5.0 | 2.5 |
| 7 | 14.5 | 11.5 |
| 10 | 31.5 | 15.8 |
| 11 | 36.0 | 19.5 |
| 12 | 13.0 | 5.5 |

EXAMPLE 1

An aqueous solution of N-acryloylpyrrolidine containing 0.5 wt. % of N,N'-methylenebisacrylamide was prepared by dissolving 507.5 g of N-acryloylpyrrolidine and 2.6 g of N,N'-methylenebisacrylamide in 1,170 g of distilled water. After chilling the aqueous solution to 10° C., it was transferred to a Dewar bottle made of stainless steel and having an internal volume of 2 l. Nitrogen gas was bubbled at a flow velocity of 1 l/mm for 1 hour through a ball filter. To the resultant aqueous solution, were simultaneously added a solution containing 2.55 g of ammonium persulfate dissolved in 0 g of distilled water and another solution containing 1.16 g of sodium hydrogensulfite dissolved in 10 g distilled water. The aqueous solution was adiabatically polymerized. After chopping the thus-obtained gel into small pieces and drying the same, it was ground further. A 20–100 mesh fraction (Tyler mesh number) was collected as a sample.

A bed pad made of a rayon and having a thickness of about 1.5 cm and a size of 120 cm × 180 cm was unsewed at an area of 80 cm × 120 cm which corresponded to the lap area of a man during its use. After uniformly spreading 25 g of the sample powder between the upper and lower layers of the pad, it was sewn as it had been so that a test sample was prepared. No unusual feeling was observed at all as to the feeling to touch and the like of the thus-obtained test sample. Its feeling to tough and the like were the same as those of the original product.

The area of the test sample, in which area the sample powder was held, was soaked with 300 ml of 0.1 N saline. Five minutes later, that area was pressed by a hand. The surface of the test sample was dry and no release of water was felt. The hand was not gotten wet at all. There was no substantial changes observed on the external appearance of the test sample after the absorption of the saline. Thereafter, the saline-soaked test sample was washed with a usual detergent, under usual conditions, in a usual electric washing machine. Its water was then removed by centrifugation. No substantial changes were observed on the external appearance of the test sample. After the water removal, the test sample was immersed in distilled water. An aqueous solution of silver nitrate was dropped into a portion of the immersing water, but clouding was not observed. It was thus confirmed that the salt had been completely removed. Thereafter, the test sample was dried at 90° C., for 30 minutes, in a usual hot air drier. The feeling to touch and the like of the test sample were not different from its feeling to touch and the like before the test. The test sample had been dried up completely.

The above-described steps of the saline absorption, washing and drying were repeated 60 times. No significant changes were however observed as to the saline absorbing and holding capacity and drying readiness of the test sample after the test.

A similar test was conducted by using 300 ml of urine in place of the above-described saline. No differences were observed compared with the results obtained above by using the saline.

COMPARATIVE EXAMPLE 1

A bed pad of the same type as that employed in Example 1 was soaked with 300 ml of 0.1 N saline at an area of 80 cm × 120 cm which corresponded to the lap area of a man during its use. Five minutes later, that area was pressed by a hand. The surface of the test sample was very wet and the hand was gotten wet immediately. The same area was again pressed by the hand one hour later. The hand was also gotten wet.

COMPARATIVE EXAMPLE 2

A sample powder was obtained by using an aqueous solution containing 400.9 g of acrylamide, 106.6 g of sodium acrylate and 2 6 g of N,N'-methylenebisacrylamide dissolved in 1,170 g of distilled water and conducting its polymerization, drying and grinding in the same manner as in Example 1. By using 25 g of the sample powder and a bed bad of the same type as that employed in Example 1, a test sample was obtained in the same manner as in Example 1. A similar test was conducted thereon. Namely, the test sample was washed after it had been soaked with 300 ml of 0.1 N saline. At the stage of its rinsing, the area where the sample powder was held was swollen considerably and the thickness of that area became significantly greater than the remaining area. The test sample was weighed. It was found that its weight increased by 8 kg compared with its weight before its washing. It was also dried by hot air under the same conditions as those employed in Example 1. Even after the drying, it had not been fully dried at the area where the sample powder was held. The thickness of that area was still greater than that of the remaining area. It was dried for a time period ten times longer than the drying time in Example 1. However, its dryness was still insufficient. Its thickness had not yet returned to the same level as the thickness of the remaining area.

EXAMPLE 2

A gel was obtained in the same manner as in Example 1 except that the initiation temperature of the polymerization was raised to 20° C. and an aqueous solution containing 4.41 g of 2,2'-azobis-2-amidinopropane hydrochloride dissolved in 20 g of distilled water was used as a polymerization initiator. After chopping the thus-obtained gel into small pieces and drying the same, it was ground further and its −100 mesh fraction was collected as a sample.

Eleven sheets (total weight: 193 g) of 30 cm×80 cm non-woven fabrics, each of which was composed of polypropylene and a rayon, were superposed. Between each two layers, 2 g of the above-obtained sample powder was evenly spread to a total amount of 20 g. On one side of the resultant composite material, a breathable polyethylene film was applied. The composite material and polyethylene film were then sewn together to provide a test sample. The test sample had no stiff feeling and its feeling to touch was good.

The test sample was soaked with 300 ml of 1 N saline. Five minutes later, the test sample was pressed by a hand. The surface of the test sample was dry and the hand was not gotten wet at all. After washing the saline-soaked test sample and then removing its water under the same conditions as those employed in Example 1, it was immersed in distilled water. An aqueous solution of silver nitrate was dropped to a portion of the immersing water. No development of cloud was observed. It was thus confirmed that the salt had been completely removed. Furthermore, the test sample was dried under the same conditions as those used in Example 1. The feeling to touch and the like of the test sample were not changed at all after the test. The test sample had been dried sufficiently.

A similar test was conducted by using human urine in place of 0.1 N saline. Exactly the same results were obtained.

COMPARATIVE EXAMPLE 3

A portion of the sample powder obtained in Comparative Example 2 was ground further and its −100 mesh fraction was collected as a sample powder. By using 20 g of the sample powder, a test sample was obtained in the same manner as in Example 3. Then, it was tested. The test sample was swollen considerably at the stage of its rinsing. Its thickness increased and the sewn parts were destroyed at several locations. Some of the sample powder had thus been lost.

EXAMPLE 3

Eleven sheets (total weight: 257 g) of 40 cm×80 cm non-woven fabrics, each of which was composed of polypropylene and a rayon, were superposed. Between each two layers, 5 g of the sample powder obtained in Example 3 was evenly spread to a total amount of 50 g. On one side of the resultant composite material, a breathable polyethylene film was applied. The composite material and polyethylene film were then sewn together.

A paper pattern, which was of such a shape that two regular triangles, one having a side of 30 cm and the other a side of 35 cm, were placed with one of the vertexes of the former triangle having been brought into a face-to-face relation with one of the vertexes of the latter triangle and the mutually-confronting vertexes were connected together with a band of 10 cm wide, was then placed on the above-prepared sewn composite material. It was cut along the paper pattern and was then sewn along its contour to provide a test sample. It is generally called "incontinence drawers". The test sample was then applied to the lap area of a male adult. While holding it in rubber-made drawers, 300 ml of 0.1 N saline was poured thereinto from the front part of his body. The saline did not leak out. When the test sample was touched by a hand 5 minutes later, its surface was dry and the hand was not gotten wet. In addition, no particular unpleasant feeling was felt while the test sample was worn. Thereafter, the test sample was washed and dried under the same conditions as those employed in Example 1. After its drying, the feeling to touch and the like of the test sample were not different from its feeling to touch and the like before the test. It had thus been fully dried.

Furthermore, the test sample was worn in the above manner and urination was actually made in the test sample. Urine did not leak out. It was absorbed and held in the test sample. In addition, no particular unpleasant feeling was felt while the test sample was worn. Thereafter, the test sample was washed and dried under the same conditions as those employed in Example 1. After its drying, the feeling to touch and the like of the test sample were not different from its feeling to touch and the like before the test. It had thus been fully dried.

EXAMPLES 4–7

Sample powders were obtained by effecting polymerization and grinding in the same manner as in Example 1 except that instead of N-acryloylpyrrolidine in Example 1, N-isopropylacrylamide (Example 4), N-n-propylacrylamide (Example 5) and N-acryloylmorpholine (Example 7) were used. Using the respective sample powders in their corresponding amounts given in Table 1, the absorption of 0.1 N saline or urine and their feeling to touch after their drying were evaluated in accordance with the testing methods shown in the table, namely, by using pads or diapers in accordance with their respective testing methods designated by Example numbers. Results are shown in Table 1.

In Example 6, the sample was prepared in the following manner, on which a similar test was conducted.

A 30% N,N-dimethylformamide solution containing 0.5% of N,N'-methylenebisacrylamide in N,N-diethylacrylamide was transferred into a Dewar bottle. After purging the liquid with nitrogen, 1.5% of azobisisobutylonitrile was added at 30° C., followed by adiabatic polymerization of the solution. The resulting gel was chopped and dried at 120° C. It was then ground to collect its 20–100 mesh fraction.

EXAMPLE 8

On a sheet of cotton gauze which had been cut into a trapezoidal shape having a lower side of 25 cm long, an upper side of 8 cm long and a height of 25 cm, was superposed a pad of polyester cotton of 80 g/m$^2$ which had also been cut into the same shape. Then, 25 of the sample powder obtained in Example 1 was spread evenly on the pad of polyester cotton. An additional pad of polyester cotton of the same shape and an additional sheet of cotton gauze of the same shape were superposed on the thus-spread sample powder, followed by their compression for 1 minute under the conditions of 120° C. and 100 kg/cm$^2$. After sewing the resultant composite material in a diamond pattern, a moisture-permeable and waterproof fabric (a polyester fabric with its one side urethane-coated) which had been cut into a trapezoidal shape having a lower side of 31 cm, an upper side of 14 cm and a height of 31 cm was brought into a contiguous relation with the sewn composite material. It was then sewn on the inner surface of a bottom part of lady drawers made of a knit cloth, thereby providing sample incontinence drawers. Upon sewing the composite material on the lady drawers, an approximately 3 cm-wide marginal portion of the moisture-permeable and waterproof fabric was folded back onto the cotton gauze.

The inside of the sample incontinence drawers was gradually soaked with 300 ml of human urine. Five minutes later, the urine-soaked area was pressed by a hand. The surface of the test sample was dry and no release of that urine was observed. The hand was not gotten wet at wall. No substantial changes were observed on its external appearance. Then, the test sample was subjected to washing and water removal under the same conditions as those used in Example 1. No unusual changes were observed during its washing. After the water removal, the weight of the test sample was measured. It was found to be 575 g. The test sample was thereafter dried at 90° C. for 30 minutes in a hot air drier. After the test sample had been dried, its feeling to touch and the like were not different at all from its feeling to touch and the like before the test. It had thus been fully dried.

Furthermore, the test sample was worn and urination was actually effected therein. No leakage of urine was observed, namely, the urine was absorbed and held in the test sample. During its use, no particular unpleasant feeling was experienced. Thereafter, the test sample was subjected to washing and water removal under the same conditions as those employed in Example 1. It was then immersed for 20 minutes in hot water of 90° C. so that it was subjected to a heating treatment. Water was thereafter removed from the test sample and its weight was measured. It was found to be 132 g. The test sample was then dried at 60° C. for 30 minutes in a hot air drier. Its feeling to touch and the like were not different at all from its feeling to touch and the like before the test. It had thus been fully dried.

EXAMPLE 9

On a non-woven rayon fabric which had been cut into a rectangular shape of 25 cm long and 14 cm wide, a non-woven polyester fabric cut into the same shape was superposed. Then, 25 g of the sample powder obtained in Example 1 was spread evenly. The resultant material was folded double along the longer sides thereof, and was then compressed for 1 minute under the conditions of 120° C. and 100 kg/cm². After sewing the resultant composite material in a diamond pattern, its outer edge portions were sewn so as to form it into a bag-like shape.

The composite material was then brought into a contiguous relation with a central part of a moisture-permeable waterproof fabric of the same shape and material as that employed in Example 8 with the upper and lower sides of composite material being in registration with those of the the trapezoidal moisture-permeable and waterproof fabric. Over the thus-combined materials, a pad of polyester cotton and a sheet of cotton gauze, each, of the same shape were successively superposed. Similar to Example 8, the moisture-permeable waterproof fabric was folded back. The resultant composite material was then sewn on the inner surface of a bottom portion of lady drawers made of a knit cloth so that sample incontinence drawers were produced.

The inside of the sample incontinence drawers was gradually soaked with 300 ml of human urine. Five minutes later, the urine-soaked area was pressed by a hand. The surface of the test sample was dry and no release of that urine was observed. The hand was not gotten wet at wall. No substantial changes were observed on its external appearance. Then, the test sample was subjected to a heating treatment under the same conditions as those used in Example 9, followed by its water removal and drying. After the test sample had been dried, its feeling to touch and the like were not different at all from its feeling to touch and the like before the test. It had thus been fully dried.

Furthermore, the test sample was worn and urination was actually effected therein. No leakage of urine was observed, namely, the urine was absorbed and held in the test sample. During its use, no particular unpleasant feeling was experienced. Thereafter, the test sample was washed and dried in the same manner and under the same conditions as those employed above. Its feeling to touch and the like were not different at all from its feeling to touch and the like before the test.

EXAMPLE 10

N-Acryloylpyrrolidine containing 1% of tertbutyl peroxy-2-ethylhexanoate was allowed to stand at 40° C. for 40 hours to effect solventless polymerization, thereby obtaining a block-like polymer. The polymer was ground and its 20–100 mesh fraction was collected as a sample powder. By using 20 g of the sample powder, a diaper-like test sample was prepared in exactly the same manner as in Example 3. A test was then carried out in the same manner as in Example 3. Test results are shown in Table 1.

EXAMPLES 11 and 12

Sample powders were obtained by conducting polymerization and grinding in the same manner as in Example 1 except that 403.0 g of N-acryloylpyrrolidine, 102.0 g of N,N-dimethylacrylamide and 5.1 g of N,N'-methylenebisacrylamide (Example 11) and 397.9 g of N-acryloylpyrrolidine, 102.0 g of N-vinyl-2-pyrrolidone and 10.2 g of N,N'-methylenebisacrylamide (Example 12) were used respectively. By using the sample powders, drawers-like test samples were produced, on which tests were carried out. Test results are also given in Table 1.

TABLE 1

| Ex. No. | Composition (wt. %) | | Used amount (g) | Testing method | Test results Absorption of 0.1 N saline or urine | Feeling to touch after drying |
|---|---|---|---|---|---|---|
| 4 | N—Isopropylacrylamide | (99.5) | 30 | Pad (saline) | O | O |
|   | N,N'—Methylenebisacrylamide | (0.5) |    | Pad (urine)  | O | O |
| 5 | N—n-Propylacrylamide | (99.5) | 40 | Pad (saline) | O | O |
|   | N,N'—Methylenebisacrylamide | (0.5) |    | Pad (urine)  | O | O |
| 6 | N,N—Diethylacrylamide | (99.5) | 70 | Pad (saline) | O | O |
|   | N,N'—Methylenebisacrylamide | (0.5) |    | Pad (urine)  | O | O |
| 7 | N—Acryloylmorphorine | (99.5) | 30 | Pad (saline) | O | O |
|   | N,N'—Methylenebisacrylamide | (0.5) |    | Pad (urine)  | O | O |
| 10 | N—Acryloylpyrrolidine | (100) | 20 | Diaper (Ex. 2) | O | O |
| 11 | N—Acryloylpyrrolidine | (79.0) | 25 | Drawers (Ex. 8) | O | Δ |

TABLE 1-continued

| Ex. No. | Composition (wt. %) | | Used amount (g) | Testing method | Test results | |
|---|---|---|---|---|---|---|
| | | | | | Absorption of 0.1 N saline or urine | Feeling to touch after drying |
| 12 | N,N—Dimethylacrylamide | (20.0) | 30 | Drawers (Ex. 9) | Δ | O |
| | N,N'—Methylenebisacrylamide | (1.0) | | | | |
| | N—Acryloylpyrrolidine | (78.0) | | | | |
| | N—Vinyl-2-pyrrolidone | (20.0) | | | | |
| | N,N'—Methylenebisacrylamide | (2.0) | | | | |

In Table 1, the test results were evaluated in accordance with the following standards.
(1) Absorption of 0.1 N saline or urine:
O: The surface of the test sample looked dry, and the hand was not gotten wet.
Δ: The surface was slightly wet, and the hand was gotten wet slightly.
(2) Feeling to tough after drying:
O: The test sample was sufficiently dry, and was not different from its conditions before the test.
Δ: The test sample was not fully dried, and it was somewhat swollen.

EXAMPLE 13

Sample incontinence drawers were produced in exactly the same manner as in Example 8 except that instead of 25 g of the sample powder obtained in Example 1, was used a mixture obtained by thoroughly stirring and mixing 25 g of the same sample powder and 2.5 g of synthetic polyethylene pulp (trade mark "SWP"; product of Mitsui Petrochemical Industries, Ltd.) having an average fiber length of 0.9 mm.

The inside of the sample incontinence drawers was gradually soaked with 300 ml of human urine. Five minutes later, the urine-soaked area was pressed by a hand. The surface of the test sample was dry and no release of that urine was observed. The hand was not gotten wet at wall. No substantial changes were observed on its external appearance. Then, the test sample was subjected to washing, water removal and drying under the same conditions as those employed in Example 1. After the test sample had been dried, its feeling to touch and the like were not different at all from its feeling to touch and the like before the test. It had thus been fully dried.

Furthermore, the test sample was worn and urination was actually effected therein. No leakage of urine was observed, namely, the urine was absorbed and held in the test sample. During its use, no particular unpleasant feeling was experienced. Thereafter, the test sample was washed and dried in the same manner and under the same conditions as those employed above. Its feeling to touch and the like were not different at all from its feeling to touch and the like before the test.

What is claimed is:

1. A urine absorbing and holding material comprising a supporting layer for a urine absorbing and holding component and a layer of a component:
said supporting layer consisting of woven or non-woven fabrics, or a woven or non-woven fabric and a moisture-permeable waterproof film or cloth;
said component being in the form of a powder, granules, flakes, fibers or a film, which is spread throughout the entire or a partial area of the supporting layer;
wherein said component is selected from the group consisting of:
(a) a homopolymer of a monomer selected from N-alkyl-or N-alkylene-substituted (meth)arcrylamides represented by the following general formula (I) or (II):

wherein $R_1$ means a hydrogen atom or methyl group, $R_2$ denotes a hydrogen atom or methyl or ethyl group, and $R_3$ is a methyl, ethyl or propyl group, or wherein $R_1$ means a hydrogen atom or methyl group and A denotes $-(CH_2)_n$, with $n=4-6$ or $-(CH_2)_2O(CH_2)_2$;

(b) a copolymer of two or more monomers selected from said N-alkyl- or N-alkylene-substituted (meth)acrylamides; or
(c) a copolymer of at least one monomer selected from said N-alkyl- or N-alkylene-substituted (meth)acrylamides and one or more hydrophilic or ionic monomers other than said N-alkyl- or N-alkylene-substituted (meth)acrylamides but copolyermizable with said N-alkyl- or N-alkylene-substituted. (meth)acrylamides;
said component being a water-insolubilized product of said homopolymer or said copolymers; and having such properties that even in the presence of a large excess of water said product shrinks and releases the absorbed water upon exposure to the atmosphere within the temperature range of 50°–120° C.

2. The urine absorbing and holding material of claim 1, wherein said monomer is an N-(meth)acryloylpyrrolidine or (N-(meth)acryloylpiperidine.

3. The urine absorbing and holding material of claim 1, wherein said monomer is selected from the group consisting of
N-Acryloylpyrrolidine;
N-Methacryloylpyrrolidine;
N-Acryloylpiperidine;
N-Methacryloylpiperidine;
N-Acryloylmorpholine; and
N-Methacryloylmorpholine.

4. A urine absorbing and holding material as claimed in claim 1, wherein the urine absorbing and holding component is spread in an amount of 5–1000 g/cm² per layer of the fibrous material or based on the whole layers of the fibrous material.

5. A urine absorbing and holding material as claimed in claim 1, wherein one or more bag-like portions are formed in some parts of a woven or non-woven fabric and the urine absorbing and holding component, which is in the form of powder, granules, flakes, fibers or a film, is held in the bag-like portions.

6. A urine absorbing and holding material as claimed in claim 1, wherein the material is a pad-like urine absorbing and holding material obtained by spreading the urine absorbing and holding component, which is in the form of powder, granules, flakes, fibers or a film, between the entire areas or some areas of layers of woven fabrics or non-woven fabrics, woven fabrics and non-woven fabrics, or a woven or non-woven fabric and a moisture-permeable waterproof film or cloth, cutting the resulting composite material into a desired shape, and then sewing, pressing or melt-bonding the thus-cut composite material.

7. A urine absorbing and holding material as claimed in claim 1, wherein the material is a diaper-like urine absorbing and holding material obtained by spreading the urine absorbing and holding component, which is in the form of powder, granules, flakes, fibers or a film, between the entire areas or some areas of layers of woven fabrics or non-woven fabrics, or a woven or non-woven fabric and a breathable film, cutting the resulting composite material into a desired shape, and then sewing, pressing or melt-bonding the thus-cut composite material.

8. A urine absorbing and holding material as claimed in claim 1, wherein the material is a drawers-like urine absorbing and holding material obtained by spreading the urine absorbing and holding component, which is in the form of powder, granules, flakes, fibers or a film, between the entire areas or some areas of layers of woven fabrics or non-woven fabrics, or a woven or non-woven fabric and a breathable film, cutting the resulting composite material into a desired shape, and then sewing, pressing or melt-bonding the thus-cut composite material.

9. A urine absorbing and holding material as claimed in claim 1, wherein the material is a pad-like urine absorbing and holding material obtained by spreading the urine absorbing and holding component, which is in the form of powder, granules, flakes, fibers or a film, together with a flocculent material, pulplike material or non-woven fabric between the entire areas or some areas of layers of woven fabrics or non-woven fabrics, or a woven or non-woven fabric and a moisture-permeable waterproof film, cutting the resulting composite material into a desired shape, and then sewing, pressing or melt-bonding the thus-cut composite material.

10. A urine absorbing and holding material as claimed in claim 1, wherein the material is a diaper-like urine absorbing and holding material obtained by spreading the urine absorbing and holding component, which is in the form of powder, granules, flakes, fibers or a film, together with a flocculent material, pulplike material or non-woven fabric between the entire areas or some areas of layers of woven fabrics or non-woven fabrics, or a woven or non-woven fabric and a breathable film, cutting the resulting composite material into a desired shape, and then sewing, pressing or melt-bonding the thus-cut composite material.

11. A urine absorbing and holding material as claimed in claim 1, wherein the material is a drawers-like urine absorbing and holding material obtained by spreading the urine absorbing and holding component, which is in the form of powder, granules, flakes, fibers or a film, together with a flocculent material, pulplike material or non-woven fabric between the entire areas or some areas of layers of woven fabrics or non-woven fabrics, or a woven or non-woven fabric and a breathable film, cutting the resulting composite material into a desired shape, and then sewing, pressing or melt-bonding the thus-cut composite material.

* * * * *